United States Patent
Bigelow

(10) Patent No.: US 6,500,387 B1
(45) Date of Patent: Dec. 31, 2002

(54) AIR ACTINISM CHAMBER APPARATUS AND METHOD

(75) Inventor: Wil Bigelow, Modesto, CA (US)

(73) Assignee: Nukuest, Inc., Modesto, CA (US)

( * ) Notice: Subject to any disclaimer, the term of this patent is extended or adjusted under 35 U.S.C. 154(b) by 0 days.

(21) Appl. No.: 09/575,848

(22) Filed: May 19, 2000

(51) Int. Cl.[7] .............................. A61L 2/00; A62B 7/08; B01D 50/00; B01D 39/00; G01N 21/01

(52) U.S. Cl. ...................... 422/24; 422/121; 422/122; 422/169; 250/432 R; 55/286

(58) Field of Search ..................... 422/22, 24, 120, 422/121, 122, 169, 171, 172, 432 R; 250/455.11, 286; 55/487

(56) References Cited

U.S. PATENT DOCUMENTS

| | | |
|---|---|---|
| 1,674,764 A | 6/1928 | Dauphinee |
| 2,279,810 A | 4/1942 | Arnott |
| 2,495,034 A | 1/1950 | Sullivan |
| 2,732,501 A | 1/1956 | Blaeker |
| 3,094,400 A | 6/1963 | Blanton |
| 3,576,593 A | 4/1971 | Cicirello |
| 3,674,421 A | 7/1972 | Decupper |
| 3,744,216 A | 7/1973 | Halloran |
| 3,745,750 A | 7/1973 | Arff |
| 3,750,370 A | 8/1973 | Brauss et al. |
| 3,757,495 A | 9/1973 | Sievers |
| 3,768,970 A | 10/1973 | Malmin |
| 3,798,879 A | 3/1974 | Schmidt-Burbach et al. |
| 3,844,741 A | 10/1974 | Dimitrik |
| 4,070,300 A * | 1/1978 | Moroni et al. .............. 252/190 |
| 4,102,654 A | 7/1978 | Pellin |
| 4,210,429 A | 7/1980 | Golstein |

(List continued on next page.)

FOREIGN PATENT DOCUMENTS

| | | |
|---|---|---|
| DE | 2461290 | 7/1976 |
| DE | 2618127 | 11/1977 |
| DE | 2732859 | 2/1979 |
| DE | 2817772 | 10/1979 |
| DE | 3637702 | 5/1988 |

OTHER PUBLICATIONS

Nagy, et al., "Disinfecting Air with Sterilizing Lamps", Heating, Piping & Air Conditioning, vol. 26., Nos. 1–12, Apr. 1954, pp. 82–87.

Steril–Air, Inc., "Steril–Air UVC Emitters Product Brochure", date unknown, entire brochure.

Steril–Air, Inc., "Guide to UVC Emitters", date unknown, entire brochure.

Philips Lighting, "Disinfection by UV–radiation", Aug., 1992, entire paper.

Westinghouse, "Sterilamp® Germicidal Ultraviolet Tubes Product Brochure", Mar., 1982, entire brochure.

Vig, UV/Ozone Cleaning of Surfaces, Treatise on Clean Surface Technology, vol. 1, 1987, pp. 1–26.

(List continued on next page.)

Primary Examiner—Robert J. Warden, Sr.
Assistant Examiner—Imad Soubra
(74) Attorney, Agent, or Firm—Bernhard Kreten

(57) ABSTRACT

An apparatus and method for ultraviolet irradiation of air for the purpose of removing contaminants from that air is disclosed. A U-shaped ultraviolet bulb enshrouded within a quartz tube provides enhanced contaminant destruction characteristics. By combining a plurality of those bulbs in a chamber that is of polished aluminum, and further combining aluminum filters therewith, added irradiation enhancement is achieved. Further provided are baffles or baffling proximate the ultraviolet bulbs that cause the air to go turbulent thus drawing the air closer to the ultraviolet bulb and further enhancing the contaminant destruction characteristics. Moreover disclosed is treatment of substrates with a chemical agent that facilitates the arrest of contaminants from the air onto the substrate for further irradiation of the contaminants from the bulbs. This further irradiation breaks down the arrested contaminants thus providing the substrate with a self-cleansing effect.

39 Claims, 10 Drawing Sheets

U.S. PATENT DOCUMENTS

| | | | |
|---|---|---|---|
| 4,255,663 A | | 3/1981 | Lewis |
| 4,666,677 A | * | 5/1987 | Ramus et al. ............... 422/177 |
| 4,750,917 A | | 6/1988 | Fujii |
| 4,788,007 A | | 11/1988 | Baron |
| 4,931,654 A | | 6/1990 | Horng |
| 4,981,651 A | | 1/1991 | Horng |
| 5,185,015 A | | 2/1993 | Searle |
| 5,200,156 A | | 4/1993 | Wedekamp |
| 5,225,167 A | | 7/1993 | Wetzel |
| 5,288,461 A | | 2/1994 | Gray |
| 5,334,347 A | | 8/1994 | Hollander |
| 5,382,805 A | | 1/1995 | Fannon et al. |
| 5,439,642 A | | 8/1995 | Hagmann et al. |
| 5,444,330 A | * | 8/1995 | Leventis et al. ............ 313/506 |
| 5,466,425 A | | 11/1995 | Adams |
| 5,492,557 A | | 2/1996 | Vanella |
| 5,523,057 A | | 6/1996 | Mazzilli |
| 5,558,158 A | | 9/1996 | Elmore |
| 5,607,647 A | * | 3/1997 | Kinkead ..................... 422/177 |
| 5,656,242 A | * | 8/1997 | Morrow et al. ............. 422/121 |
| 5,730,770 A | | 3/1998 | Greisz |
| 5,817,276 A | * | 10/1998 | Fencl et al. ................... 422/24 |
| 5,853,676 A | | 12/1998 | Morgan, Jr. |
| 5,935,525 A | * | 8/1999 | Lincoln et al. ............. 422/177 |
| 5,948,355 A | * | 9/1999 | Fujishima et al. .......... 422/177 |
| 5,993,738 A | * | 11/1999 | Goswani ..................... 422/121 |
| 5,997,619 A | * | 12/1999 | Knuth et al. ................ 422/121 |
| 6,053,968 A | * | 4/2000 | Miller ......................... 422/121 |
| 6,221,314 B1 | * | 4/2001 | Bigelow ...................... 422/24 |

OTHER PUBLICATIONS

Jensen, "HVAC Technology is Weapon in Fight Against Tuberculosis", *ASHRAE Journal*, Aug., 1997, p. 12.

Georgia Tech Research Corporation, "Emissions from Mold and Fungus May Cause Indoor Air Problems", 1996, entire article.

Ward, "Is Your child Allergic to School—Literally?", www.townonline.com, Jan. 1997, entire article.

Layton, "Allergy & Attention Deficit Hyperactivity Disorder (ADHD)", www.allergyconnection.com, 1996, entire article.

Krajick, "The Floating Zoo", *Discover*, Feb., 1997, pp. 66–73.

Sacramento Municipal Utility District, "Water Water Everywhere, But . . . ", *On Center*, Second Quarter, 1997, p. 1.

Bayer, et al., "Study Suggests Some VOCs Caused by Molds and Fungi", *ASHRAE Journal*, Oct., 1996, p. 12.

\* cited by examiner

AIR ACTINISM CHAMBER APPARATUS AND METHOD

FIELD OF THE INVENTION

This invention relates generally to air cleansing devices. More particularly, this invention relates to ultraviolet (UV) irradiation and filtration devices. In particular, the invention deals with the use of ultraviolet radiation to decompose organic molecules that have a tendency to colonize filters and evaporation coils that are utilized to condition the air in enclosed surroundings. Also, the invention deals with the placement of ultraviolet lamps placed within a chamber that has a means for passing air therethrough. The chamber's walls are polished and as such the UV radiation emitting from the UV lamps is reflected off the chamber walls which results in the decay of organic particles adjacent and within the surround and contained therein. Further, baffles adjacent the UV lamps in the chamber cause turbulence within the air passing therethrough which results in an increase in decay of the organic molecules.

BACKGROUND OF THE INVENTION

Ultraviolet (UV) light in the form of germicidal lamps has been used since the early 1900's to kill the same types of microorganisms that typically cause the same types of problems today. Since then, UV radiation in the short wave or C band range (UVC) has been used in a wide range of germicidal applications to destroy bacteria, mold, yeast and viruses. After World War II, the use of WVC rapidly increased. UVC is generally understood to exist in the 180 nm to 280 nm wave length area. Typical examples included hospitals, beverage production, meat storage and processing plants, bakeries, breweries, pharmaceutical production and animal laboratories; virtually anywhere microbial contamination was of concern. Early UVC strategies primarily consisted of an upper air approach. This method directed a beam across the ceiling of a room.

During the 1950's when tuberculoses infections were on the rise, the use of UVC became a major component in the control and irradiation of TB. It was discovered that by placing UVC lamps in the air handling equipment, they could initially be more effective.

However, certain conditions found within the air handling systems drastically reduced UVC performance. Moving air, especially below 77° F., over the tubes decreased the output and service life of conventional UVC products and thus their ability to destroy viable organisms. The use of UVC with airflow systems virtually disappeared over the next decade due to the introduction of new drugs, sterilizing cleaners and control procedures combined with the performance problems of UVC lamps and air handling systems (reduced output, short tube life, and high maintenance). In order for UVC to be effective in the "hostile" environment of indoor central air circulating systems (or HVAC systems), a new method of producing effective UV had to be developed.

The ability of ultraviolet light to decompose organic molecules has been known for a long time, but it is only recently that UV cleaning of surfaces has been explored. In 1972, it was discovered that ultraviolet light could clean contaminated surfaces. Plus, it was learned that there is a predictable nanometer location of absorption of ozone and organic molecules. It was then learned that the combination of ozone and UV could clean surfaces up to two thousand times quicker than one or the other alone. However, from testing it can be seen that the destructive potential of a combination of UVC and ozone for system components is detrimental. The negative side effects of ozone are now known.

In 1972, tests were conducted using a quartz tube filled with oxygen. A medium pressure mercury (Hg) UV source which generated ozone was placed within centimeters of the tube. A several thousand angstrom thick polymer was exposed to this and was depolymerized in less than one hour. The major products of this reaction were water ($H_2O$) and carbon dioxide ($CO_2$). It was discovered that UV (300 nm and below) and oxygen played a major role in depolymerization. In 1974, research concluded that during such cleaning, the partial pressure of $O_2$ decreased and that of $CO_2$ and $H_2O$ increased, suggesting breakdown.

It was also discovered that the absorption coefficient of $O_2$ increases rapidly below 200 nm with decreasing wave lengths. A 184.9 nm wave length (optimal spectral line for ozone generation) is readily absorbed by oxygen, thus leading to the generation of ozone ($O_3$). Ozone may be generated at undetectable levels at other wave lengths below 200 nm. Therefore, radiation emission below 200 nm was found undesirable.

Similarly, most organic molecules have a strong absorption band between 200 nm and 300 nm. A wave length of 253.7 nm is useful for exciting and disassociating contaminant molecules. 265 nm was thought to be the optimal spectral line for germicidal effectiveness. The 253.7 nm wave length is not absorbed by $O_2$; therefore, it does not contribute to ozone generation, but it is absorbed by most organic molecules and by ozone ($O_3$). Thus, when both wave lengths are present, ozone is continually being formed and destroyed. Unfortunately, previously existing lamps operated between 250 nm and 258 nm, peaking at 254 nm, missing out on the optimal 265 nm goal.

As indicated above, the effective killing power of UV seemed to be greatest at 265 nm. However, conventional UV has its maximum intensity at 254 nm. Furthermore, the intensity degrades as a function of temperature and distance. This was due to the conventional tubes being designed as long, straight lamps.

With regard to HVAC systems, biological contaminants are difficult to control because they grow in our moist, indoor environment. The most common strategy is to try to use an effective air system filter to rid indoor air of biological contaminants. While this is an important element of cleaning air, this has its problems. Most filters are inadequate because of the many organisms that pass right on through the filter. Also, any organisms that collect on the filter can form germ colonies that may soon contaminate passing air. Further, if the filter should be too efficient, it blocks the passage of air and creates back pressure, causing the blower to struggle to move air through the system. Furthermore, when the system is turned off, natural temperature differences between the system and indoor air spaces cause convection or back draft flow into the supply ducts (bypassing the filter). This causes contaminants to be pulled back into the duct work, implanting microbes in the air flow duct cavity. These new cultures become added sources of contaminant.

In the past, to try to eliminate the biological contaminants in ducts, a common strategy was to clean the ducts followed by a biocide treatment. But this has its draw backs also. Most biological contaminants return and are active in the treated area within three months. Further, if the system is being treated for severe contamination such as legionela, an acid wash of the coil is common. This is not only expensive, but can shorten the life of the equipment. Furthermore, all biocide used in the ducts are chemical based, leaving potential toxic vapors and chemical pollutants circulating in the system as well. For obvious health reasons, the preferred way to control biological contaminants is through natural, non-polluting strategies.

The term "air-conditioning" (A/C) normally refers to cooling the air of a building. An A/C system operates like this: the outdoor portion of the A/C unit compresses a gas to a liquid. During this compression, heat energy is driven out of the liquid. This colder liquid then travels through tubing to the evaporative coil located inside the building proximate the central/furnace fan.

The evaporation coil has numerous rows of fins. The fins are all made of an aluminum alloy that is extremely tough due to an impervious film of oxide on the metal. The fins act as heat exchangers with the circulating air within the system. When this compressed liquid reaches the evaporative coil, the liquid expands and evaporates, converting back to a gas. As it does, it recovers the amount of heat energy lost in the compression cycle. This conversion absorbs heat through the coil fins from the surrounding air that is moving across the fins.

With the blower operating, air moves across the coil fins and is cooled by losing its heat to the evaporation process inside the coil.

If for some reason the central air system becomes less efficient during its operational life, the energy consumption and costs will rise. Since so much energy is involved just in normal use, any change in efficiency will mean a sharp increase in costs.

The evaporative coil is made of tiny, closely fitting fins for cooling the air. These fins are so close, the coil essentially becomes a filter, screening out and collecting dust particles from the air. Indoor airborne organic particles and microorganisms are primarily byproducts of human, animal, insect and microbial output (dead skin, hair, paint flakes, insect feces, carpet fibers, etc.) within the indoor environment. As these particles build up, the space between the fins becomes blocked, thus reducing airflow and restricting cooling efficiency of the coil.

The coil not only collects these particles, but also becomes a bio-nursery for mold and bacteria. When the A/C operates, water condenses onto the evaporative coil fins. This water drains off into a drip pan. Depending on the amount of moisture within the air, the amount of water collected and drained can be typically six gallons per day.

The evaporative coil is mounted in line to the furnace fan housing. Because of its location, the coil housing is very dark and moist. Thusly, it becomes an ideal nursery for the growth of bacteria and mold. Those skilled in the art consider the coil as the number one source of mold in homes.

At the coil, volumes of organic contaminates collect in two ways: (a) mold and bacteria growth in the damp coil produces sticky enzyme materials for trapping airborne organic material for food (this forms an activated crusty surface on the fins), and (b) the close fitting coil fins collect airborne particles much like a filter.

When the mold colonies grow on the coil, they produce a sticky substance called enzyme mycelium. Enzymes break down proteins and organic compounds. The enzyme mycelium performs two essential functions for molds: (a) the stickiness traps dust particles from the air, and (b) enzymes break the trapped particles into food.

With the dust and enzyme material collecting on the coil, an insulation film covers the fins. This installation prevents an efficient heat exchange between the air and fins and efficiency drops. With such restrictions, the cost of operating a coil can increase by 60%.

Thus, as can be seen, the coil then becomes a major source of airborne contamination (mold spores, enzymes, toxins and bacteria) due to the growth of mold, bacteria at the coil.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| U.S. PAT. NO. DOCUMENTS | | |
| --- | --- | --- |
| U.S. PAT. NO. | ISSUE DATE | INVENTOR |
| 1,674,764 | June 26, 1928 | Dauphinee |
| 2,279,810 | April 14, 1942 | Arnott |
| 2,495,034 | January 17, 1950 | Sullivan |
| 2,732,501 | January 24, 1956 | Blaeker |
| 3,094,400 | June 18, 1963 | Blanton |
| 3,576,593 | April 27, 1971 | Cicirello |
| 3,674,421 | July 4, 1972 | Decupper |
| 3,744,216 | July 10, 1973 | Halloran |
| 3,745,750 | July 17, 1973 | Arff |
| 3,750,370 | August 7, 1973 | Brauss, et al. |
| 3,757,495 | September 11, 1973 | Sievers |
| 3,768,970 | October 30, 1973 | Malmin |
| 3,798,879 | March 26, 1974 | Schmidt-Burbach, et al. |
| 3,844,741 | October 29, 1974 | Dimitrik |
| 4,102,654 | July 25, 1978 | Pellin |
| 4,210,429 | July 1, 1980 | Golstein |
| 4,255,663 | March 10, 1981 | Lewis |
| 4,750,917 | June 14, 1988 | Fujii |
| 4,788,007 | November 29, 1988 | Baron |
| 4,931,654 | June 5, 1990 | Horng |
| 4,981,651 | January 1, 1991 | Horng |
| 5,185,015 | February 9, 1993 | Searle |
| 5,200,156 | April 6, 1993 | Wedekamp |
| 5,225,167 | July 6, 1993 | Wetzel |
| 5,288,461 | February 22, 1994 | Gray |
| 5,334,347 | August 2, 1994 | Hollander |
| 5,382,805 | January 17, 1995 | Fannon, et al. |
| 5,439,642 | August 8, 1995 | Hagmann, et al. |
| 5,466,425 | November 14, 1995 | Adams |
| 5,492,557 | February 20, 1996 | Vanella |
| 5,523,057 | June 4, 1996 | Mazzilli |
| 5,558,158 | September 24, 1996 | Elmore |
| 5,656,242 | August 12, 1997 | Morrow, et al. |
| 5,730,770 | March 24, 1998 | Greisz |
| 5,817,276 | October 6, 1998 | Fencl, et al. |
| 5,853,676 | December 29, 1998 | Morgan, Jr. |

| FOREIGN PATENT DOCUMENTS | | | |
| --- | --- | --- | --- |
| PATENT NO. | COUNTRY | PUBLICATION DATE | APPLICANT |
| 2,461,290 | Germany | July 1, 1976 | Bohnensieker |
| 2,618,127 | Germany | November 10, 1977 | Bohnensieker |
| 2,732,859 | Germany | February 1, 1979 | Wagner |
| 2,817,772 | Germany | October 31, 1979 | Metallw |
| 3,637,702 | Germany | May 19, 1988 | Fuchs |

OTHER PRIOR ART (Including Author, Title, Date, Pertinent Pages, Etc.)

Nagy, et al., "Disinfecting Air with Sterilizing Lamps", *Heating, Piping & Air Conditioning*, Vol. 26., Nos. 1–12, April 1954, pp. 82–87.

Steril-Air, Inc., "Steril-Air UVC Emitters Product Brochure", date unknown, entire brochure.

Sterile-Air, Inc., "Guide to UVC Emitters", date unknown, entire brochure.

Philips Lighting, "Disinfection by UV-radiation", August, 1992, entire paper.

Westinghouse, "Sterilamp® Germicidal Ultraviolet Tubes Product Brochure", March, 1982, entire brochure.

Vig, "UV/Ozone Cleaning of Surfaces, *Treatise on Clean Surface Technology*, Vol. 1, 1987, pp. 1–26.

Jensen, "HVAC Technology is Weapon in Fight Against Tuberculosis", *ASHRAE Journal*, August, 1997, p. 12.

Georgia Tech Research Corporation, "Emissions from Mold and Fungus May Cause Indoor Air Problems", 1996, entire article.

Ward, "Is Your Child Allergic to School—Literally?", www.townonline.com, January, 1997, entire article.

Layton, "Allergy & Attention Deficit Hyperactivity Disorder (ADHD)", www.allergyconnection.com, 1996, entire article.

Krajick, "The Floating Zoo", *Discover*, February, 1997, pp. 66–73. Sacramento Municipal Utililty District, "Water Water Everywhere, But . . . ",*On Center*, Second Quarter, 1997, p. 1.

Bayer, et al., "Study Suggests Some VOCs Caused by Molds and Fungi",*ASHRAE Journal*, October, 1996, p. 12.

SUMMARY OF THE INVENTION

An air cleaning apparatus is disclosed including UV lamps, aluminum filters, and a polished aluminum housing. The UV lamps include a U-bend crystal of quartz, ruby, or sapphire contained within a quartz sleeve. Useful substances for containment within the U-bend bulb are mercury, argon, gallium, iron, xenon or krypton. Between the sleeve and lamp, certain gases (nitrogen or atmospheric gases) are contained therein or the area is possibly evacuated. There are advantages and disadvantages to each. By using a mixture of above gases and/or by varying the electrical charge, one can increase the bandwidth to about 240 nm to about 280 nm, including the 265 nm optimum wave length. Further, increased electrical charge can increase bandwidth and spectral line output from 240 nm to 360 nm for more germicidal effect (UVC/UVB).

Polished aluminum filters and chamber walls are also included in this invention. The treated, polished aluminum alloy provides enhanced reflectivity for the UV rays to enhance the irradiation of particulate flowing through the filters and by the lamps. The aluminum filters have an additional special feature in that one side of the filter is of a coarse mesh whereas the other side of the filter is of a fine mesh. Air flow is from the coarse side to the fine side of one filter, past the UV bulbs, through the fine side, and out the coarse side of another aluminum filter and then back into the duct work of an HVAC system. By providing treated, polished aluminum surfaces surrounding the UV lamps, irradiation is enhanced significantly.

An alternate embodiment in the form of a portable air cleaning device is also described herein. The purpose of the portable device is to clean a single room with a similar system as described hereinabove, but also including a fan built into the portable unit to move through the system.

Another embodiment is described wherein a UV lamp array is mounted exterior to a compressor coil of an HVAC system thereby allowing for cleansing of contaminants contained on the coil and fin structure of the compressor. It has been known that this is a breeding ground for microorganisms and cleansing of this breeding ground will enhance cleansing of the entire HVAC system.

By inserting an UVC lamp into the coil region and adding a chemical catalyst, a process of organic "dusting" and microbial cleaning takes place at the coil. The process is further enhanced because the aluminum fins are excellent reflectors of the ultraviolet within the coil chamber resulting in UV amplification, with little or no deterioration on the metal itself.

As the air passes the WVC lamp, electrons of a dust, toxins, and microorganism molecules are ejected. Electrons are negative. When the electrons are ejected a positive particle or ion is left behind.

As the circulating air pass through the coil fins, the aluminum oxide fins pick up the charged organic and biological materials coming from the UV light area. The organic material adheres to the aluminum fins for several reasons.

The oxide film in the aluminum has a high propensity to collect electrons that generates an electrostatic polarity. This produces an affinity for either negative or positive ions (depending upon the pH) to the coil fins. Aluminum oxide has the highest advantage over all solid material because it is very stable over a wide range of pH. Normally the pH on the fin surface will be relatively high from the decay of organic materials on the fins, thus attracting positive ions to the coil.

The process on the aluminum oxide mesh is called electronegativity, which forms the basis of electrostatic energy on the filter surface. Electronegativity is based upon the principle of the power of an atom in a molecule to attract elections to itself. The electronegativity of an element depends upon its valence state. Aluminum has an average electronegativity value of 1.61 (near the middle compared to the other element values in the group); oxygen has the second highest value of all elements to attract electrons to itself at 3.44. All coil fins are made of aluminum oxide metal, thus having a very high attraction ability of free electrons to the fins, primarily due to the strength of the oxide (oxygen) to attract elections.

The aluminum oxide fins have an enormous capacity to attract an abundance of free electrons stripped by the UV from the incoming organic and biological particles before getting to the coil. As the aluminum oxide collects more and more electrons, the coil loads up on electrons, becoming primarily negative.

And as the positively charged organic ion material (coming from the UV light area) nears the negatively charged coil, the organic molecules begin adhering to the fins based upon the principle of positive/negative polarity (the electrostatic principle). In other words, the incoming airborne positively charged organic materials are attracted to the negatively charged coil and adhere to the coil fins.

With the dust adhering to the coil fins, the UVC can then begin the breakdown process. The invention then has two methods of breaking apart the hydrocarbon contaminates.

The damaging effects of x-ray and gamma ray radiation are recognized but not fully understood. X-ray, gamma, ultraviolet, infrared and visible light energy fit in a category called electromagnetic energy. They all have the same characteristic of an oscillating energy wave that travels at the speed of light. The difference in each type of wave energy is the wavelength or the distance across the wave. The shorter the distance across the wave body, the shorter the wavelength and the stronger the energy. It is this wavelength difference that results in short-wave x-ray passing through walls, while longer wave lengths of visible light cannot. Short-wave ultraviolet and x-ray can destroy DNA in living microorganisms and break down organic material while visible light cannot.

The science of ultraviolet radiation usage is essentially the science of photochemistry. Photochemistry is defined as a chemical reaction or change in a material induced by the radiation of light energy.

The photochemical process takes place when electrons of a molecule are ejected or changed by the irradiation of light energy, leaving an incomplete and decaying molecule. With the absence of an electron, organic compounds become unstable and fall apart.

All organic particles and microorganisms have a strong reaction to light energy between 180–320 nm. Such molecules are vulnerable to short-wave UV irradiation. The reason: molecular structures depend upon the continued maintenance of a molecular weight. But this weight is altered when UV irradiation reduces the number of electrons orbiting an organic molecule. This causes decay of the material.

Ultraviolet radiation in the C-band (WVC) has properties that alter the cells of living tissue, particularly microbes due to size. WVC radiation ejects electrons and alters the bonds between amino acids in the microbe's DNA molecules. This renders bacteria, viruses and molds sterile. The cell structure of microbes will continue to degrade in the presence of short-wave UV and will break down into free state ions and/or separate carbon or hydrogen molecules.

One of the reactions is the formation of hydrogen peroxide ($H_2O_2$) from the photochemical change of the dust, toxins and microorganism collecting at the coil. When the UV changes molecular electrons of the organic material often hydrogen is ejected from the molecules of the material. These hydrogen radicals then react with ordinary atmospheric oxygen ($O_2$), forming hydrogen peroxide $H_2O_2$. The hydrogen peroxide process activates a chain reaction, oxidizing organic material and helping to clean coil surfaces.

Further, the hydrogen peroxide is also converted to hydroxide (OH—), which is a very powerful oxidizing agent.

At the factory or before the coil is installed, the evaporative coil fins are sprayed with a liquid mixture of water and sodium persulfate ($Na_2S_2O_8$), or potassium persulfate ($K_2S_2O_8$) or sodium hydroxide (NaOH). These liquid mixtures dry at room temperature on the surface of the coil fins, leaving a residue of the persulfates or sodium hydroxide.

The persulfates, when exposed to UV at wavelengths 100 nm to 320 nm, forms hydrogen peroxide ($H_2O_2$). Hydrogen peroxide, however, quickly breaks down into hydroxide (OH) and water ($H_2O$) when exposed to these UV wavelengths.

Under the alternative, the sodium hydroxide, when exposed to short wave ultraviolet, breaks down into sodium (Na) and hydroxide (OH).

The dried crystals of persulfates within the coil fins, when exposed to UV form by products including hydrogen sulfate and hydrogen peroxide ($S_2O_8^{-2}+2H_2O+UV=2HSO_4^-+H_2O_2$). The hydrogen peroxide ($H_2O_2$) both hydroxide (OH) and water in the presence of UV ($H_2O_2+UV=H_2O+OH$).

The hydroxide formation is from the UV and persulfates (persulfates to hydrogen peroxides converting to hydroxide in the presence of short wave to medium wave UV) or the sodium hydroxide that have been sprayed on the coil fins. In either case hydroxide is formed in the presence of UV.

Hydroxide is a stable but a very potent one-electron oxidant. The reason hydroxyl ions are so destructive to organic molecules (house dust, toxins and microorganism) is the hydroxide ions "capture" hydrogen molecules from the organic materials, leaving decayed carbon ions. The removal of hydrogen from organic molecules by hydroxide forms even stronger reactive OH bonds as the result of the water at the coil. The process turns into a chain reaction, resulting in continual decay of the organic material by hydroxide formation and converting back to water.

Hydroxide primarily targets organic materials for oxidation. This oxidizing agent thrives by absorbing hydrogen from organic compounds. Hydroxide is perhaps the ideal oxidizer for cleaning organic growth in the evaporation coil without the corrosive effects of ozone. A damp coil is the best environment to experience the full effects of UV. It is in this promising condition that UV energy breaks down the collected organic material, setting off a chain reaction of hydroxide and hydroperoxide formation, which further destroys organic materials.

This means the invention effectively cleans the evaporation coil of organic particle collection and destroys any growth of germs and mold accumulating at the coil. Once clean, the coil remains clean in the presence of the invention.

OBJECTS OF THE INVENTION

Accordingly, it is a primary object of the present invention to provide an ultraviolet ray actinism chamber for destroying contaminants thereby.

Another object of the present invention is to avoid the production of ozone in such a system.

Another object of the present invention is to provide increased UV bandwidth to so increase the "killing" power of the UV system.

Another object of the present invention is to maintain a substantially constant temperature around the UV bulb.

Another object of the present invention is to increase UV reflectivity in and around the UV bulbs to enhance the UV irradiation.

Another object of the present invention is to provide self cleaning filters for a UV system.

Another object of the present invention is to provide better, yet shorter lamp lengths to fit in conventional HVAC systems.

Yet another object of the present invention is to enhance the bulb life of a UV bulb for such a system.

Viewed from a first vantage point, it is an object of the present invention to provide an apparatus for purging impurities from ambient air conditions, comprising: a source of radiation in operative communication with the ambient air conditions; and a coating upon which radiation emitted from said source impinges thereon facilitating a chemical reaction.

Viewed from a second vantage point, it is an object of the present invention to provide an a method for purging impurities from ambient air conditions, comprising the steps of: creating turbulent air around an ultraviolet light source; passing the turbulent air adjacent to the ultraviolet light source to create a photochemical reaction.

Viewed from a third vantage point, it is an object of the present invention to provide a self-cleansing filter or evaporative coil prepared by a process comprising the steps of: coating a substrate with a mixture of water and sodium hydroxide or a persulfate; drying the mixture coated in the substrate at room temperature leaving a residue of the persulfate or sodium hydroxide Viewed from a fourth vantage point, it is an object of the present invention to provide a chamber for cleansing ambient air, comprising, in combination: an air inlet; an air outlet; said chamber interposed and communicating between said inlet and outlet; a source of radiation in said chamber, said chamber imperforate to the radiation; said chamber having an interior surface with means for reflecting substantially all the radiation; and a coating means to enhance the effect of the radiation.

Viewed from a fifth vantage point, it is an object of the present invention to provide a method for coating a filter mesh or an evaporative coil for providing either negative or positive ions depending upon the pH or pOH, the steps comprising: forming a filter mesh or evaporation coil out of aluminum; dipping or spraying the filter mesh or evaporation coil with a liquid mixture to form a film; wherein the liquid mixture is selected from the group consisting of water and sodium persulfate, potassium persulfate and sodium hydroxide.

Viewed from a sixth vantage point, it is an object of the present invention to provide an method of photochemically treating ambient air to purge impurities, the steps comprising: filtering the air; exposing the air to a source of radiation; further filtering the air after exposure to radiation to arrest irradiated particles within the air after irradiation; and further exposing the arrested, irradiated particles to further radiation causing a break down of the molecular structure of said irradiated particles that yields a self-cleansing effect to a structure to which the arrested, irradiated particles were arrested by.

Viewed from a seventh vantage point, it is an object of the present invention to provide a method of treating air with a chemical disposed on an aluminum substrate, the steps comprising: passing air through the aluminum substrate in order to arrest particles or organic molecules; exposing the particles or organic molecules to radiation to cause breakdown of the molecular structure in order to remove particles or organic molecules from the aluminum substrate thus providing a self-cleansing effect.

These and other objects will be made manifest when considering the following detailed specification when taken in conjunction with the appended drawing figures.

DESCRIPTION OF PREFERRED EMBODIMENTS

Figure 1:
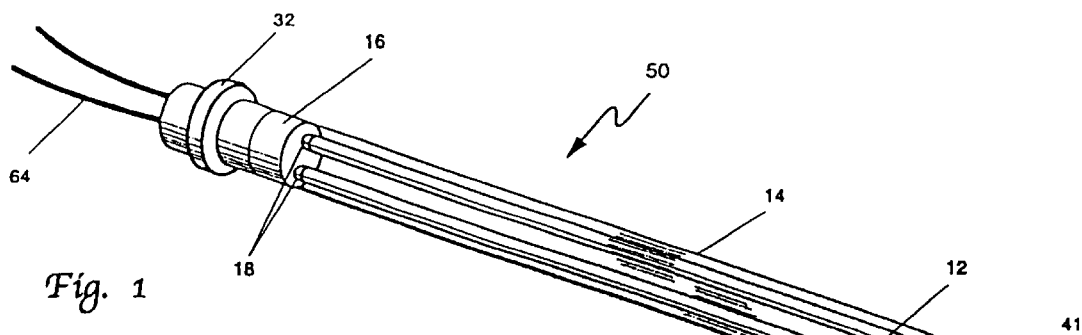
FIG. 1 is a perspective view of the UV lamp of the invention.
Figure 2:
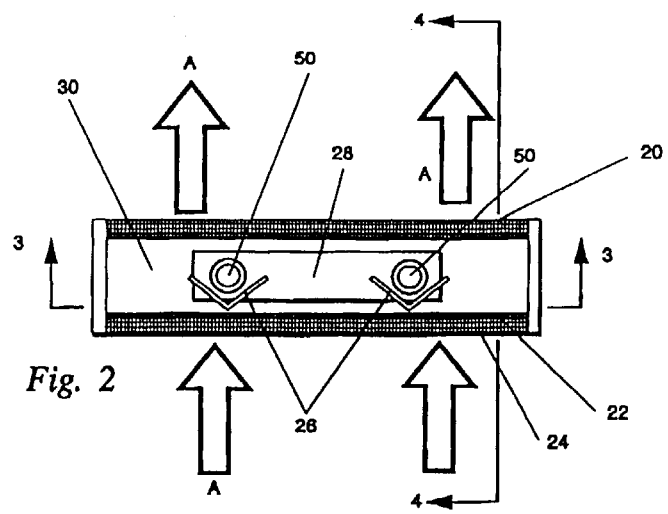
FIG. 2 is a top view of an embodiment of the invention.
Figure 2A:
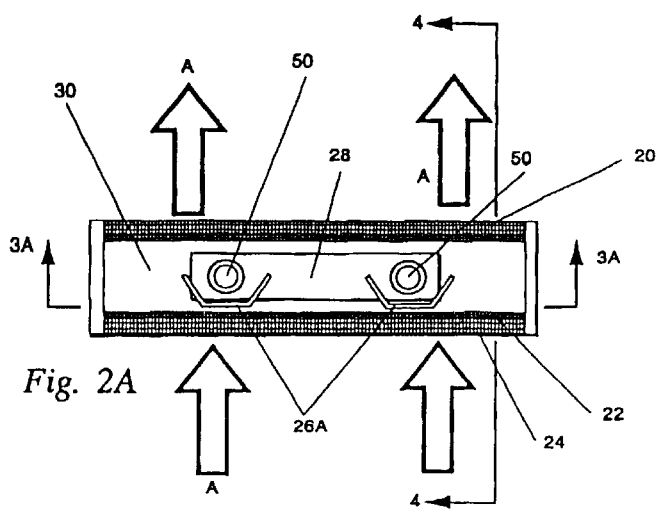
FIG. 2A is a top view of an alternative embodiment of the invention
Figure 3:
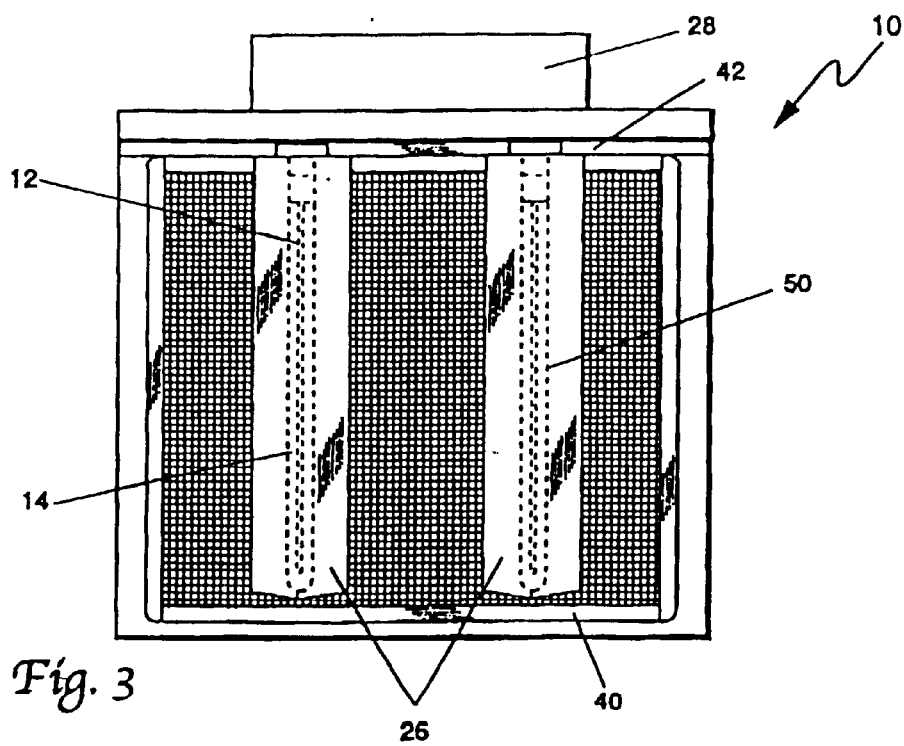
FIG. 3 is a cross-sectional front view taken along lines 3—3 of FIG. 2.
Figure 3A:
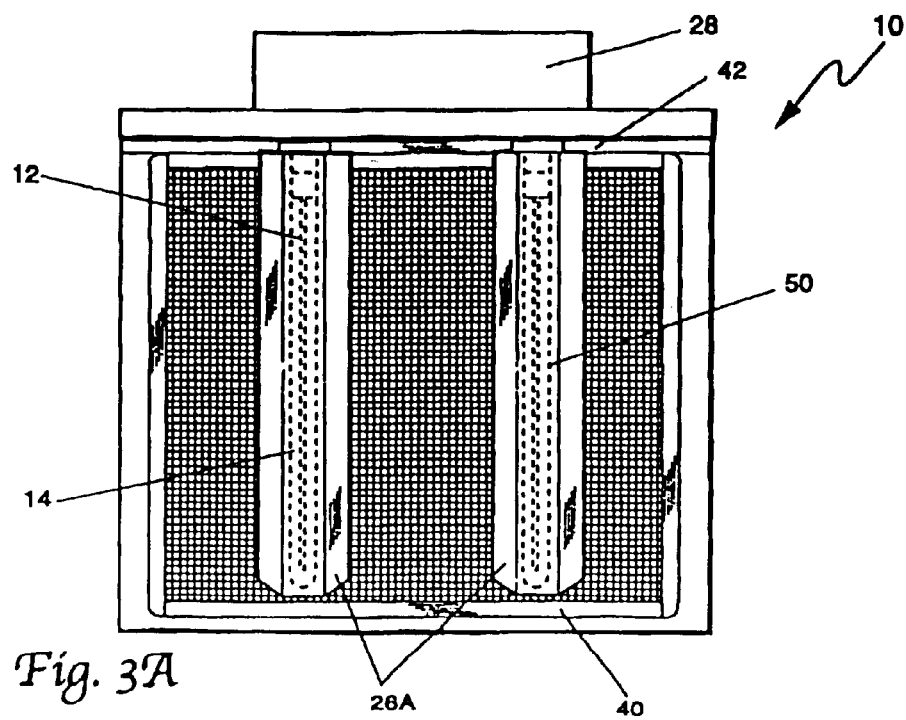
FIG. 3A is a cross-sectional front view taken along lines 3A—3A of FIG. 2A

Considering the drawings, wherein like reference numerals denote like parts throughout the various drawing figures, reference numeral 10 is directed to the air actinism chamber according to the present invention.

The invention relies on four main components: UV lamp 50, photon chamber 34, baffles 26 or 26A and filters 20. Each component will be described more particularly below.

Figure 8:
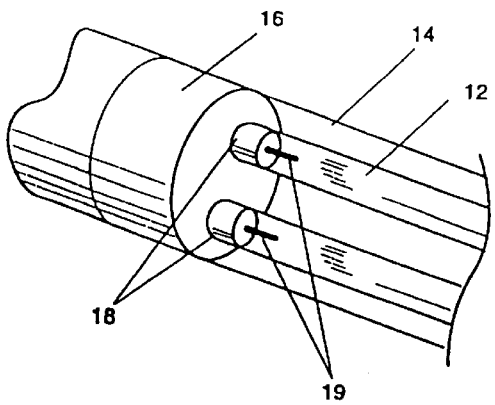
FIG. 8 is a perspective view of the electrode connection of the invention.

As seen in FIGS. 1 and 8, UV lamp 50 consists of a U-shaped UV quartz, ruby, or sapphire crystal 12 (with quartz being preferred), a quartz sheath 14, lamp coupling overlay 16, lamp base 32, U-shaped bulb gases 41, and lamp gas 44. U-shaped bulb 12 is preferably a quartz glass tube up to fifty inches long that is bent at the center to form a U-shaped bulb filled with one or more of the following: mercury, argon, iron, gallium, xenon or krypton. Aluminum metal or ceramic material is machined for the base 32 of the lamp for holding both the lamp tube 12 and electrode igniters 18. An aluminum coupling 16 allows for good heat transference resulting from the heating of electrodes 18 inside the aluminum coupling 16. That convection heat will be used to maintain its own stabilizing environment around the U-shaped bulb 12 and within the quartz sheath 14 regardless of ambient temperatures.

Once the U-shaped bulb 12 is mounted onto the aluminum coupling 16 at the point where electrodes 18 extend from within the coupling 16, a gas or gas mixture is sealed within quartz sheath 14. That gas or gas mixture is preferably comprised of nitrogen, ordinary air, or evacuated space. By using just air, an approximately 3% loss of intensity of UV is suffered, but certain other costs are lessened. The 3% loss could be eliminated by evacuating the space, however, heat convection does not work as well without gases. Nitrogen gas hermetically sealed under the quartz sheath 14 seems to be best, but manufacturing is more complicated.

Figures 4, 5:
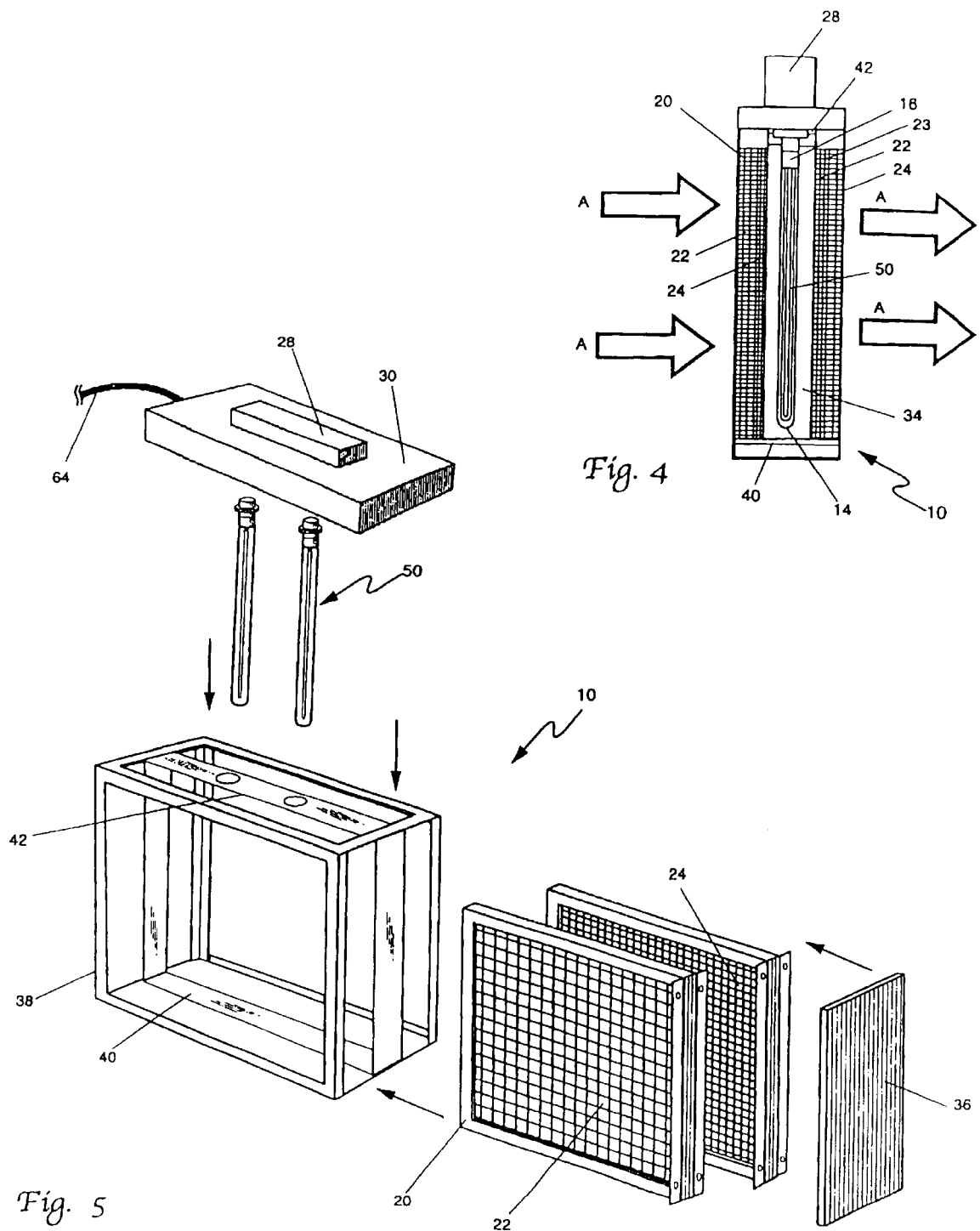
FIG. 4 is a cross-sectional side view taken along lines 4—4 of FIG. 2.
FIG. 5 is an exploded parts perspective view of the invention.

By sealing the U-shaped quartz bulb 12 within quartz sheath 14, a constant temperature around bulb 12 is maintained at approximately 80° F. to 90° F. This has been found to be the case even when ambient air temperatures are as low as 45° F. The entire lamp 50 coupled to a proper power supply, as seen in FIGS. 1 and 5, then, for all normal intents and purposes, has the ability to maintain the highest level of intensity regardless of surrounding air temperature or air speed.

UV lamp 50 provides a broader bandwidth compared to conventional UV lamps. As described above, conventional UV lamps emit a bandwidth of about 250 nm to 258 nm. UV lamp 50 provides a bandwidth of about 240 nm to 280 nm, including the optimal 265 nm wavelength and provides approximately six times the UV intensity of conventional lamps at colder temperatures. Furthermore, this is achieved while ambient air temperature around UV lamp 50 is 45° F. to 90° F. Although more power may be required, it has also been discovered that operation at "medium-pressure" will achieve a bandwidth of 230 nm to 380 nm, with an excellent spike at 264 nm. Another optimum point has also been discovered between 310 nm and 340 nm. So, although greater power, and therefore cost, may be required, greater particulate destruction is possible.

The chamber is shown in FIGS. 2 through 5. Lamps 50 are then mounted into housing 28 that includes the electronics and power supply to drive the lamps 50. The power supply is preferably either a matched 110 or 220 volt AC input power supply having a power cord 64. To start the lamp, the power supply sparks the UV gas core 44 and ignites it from a cold start with a temporary voltage spike of about 3,000 volts passing through electrodes 18 and wires 19 (see FIG. 8) to the substances contained within bulb 12. Once the substances are ignited by this starting voltage, the power supply output voltage adjusts down to an operating voltage of about 200 volts to 240 volts AC. By inserting lamps 50 into a chamber of an HVAC unit, UV irradiation of air flowing over and by the lamps 50 is achieved. However, the actinism in the chamber can be enhanced by using special aluminum filters 20 and reflective surfaces within chamber 34.

UV ray reflection can be accomplished by several surface types. Magnesium Oxide, for instance, has been found to achieve the greatest reflectivity (75% to 90%), but is not suited for normal use due to its negative properties. Polished aluminum alloy (treated with Alzak), on the other hand, can achieve up to 95% reflectivity and is well suited to production and manufacture. Typical duct liner reflects 0% to 1% of UV rays which is a draw back of the prior art. Even stainless steel only achieves 25% to 30% reflectivity. Therefore, treated aluminum alloy is preferred.

Figure 10:
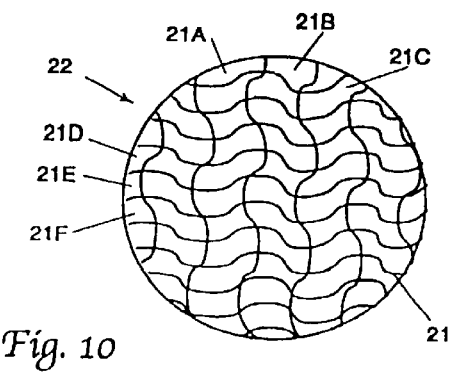
FIG. 10 is a top cutaway view of the coarse filter weave.
Figure 11:
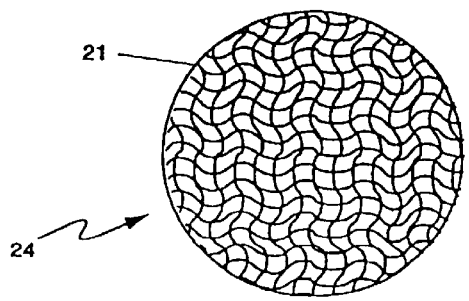
FIG. 11 is a top cutaway view of the fine filter weave.

First, with regard to the filters, a two layered filter constructed of buffed aluminum is preferred. A first coarse layer 22 on an outside of the filter 20 and a second fine mesh layer 24 on the inside of the filter is preferred, wherein the mesh is a wavy aluminum strand weave 21 (FIGS. 10 and 11). That weave may also consist of ribbons of aluminum strands 21A, 21B, 21C interwoven with other such ribbons 21D, 21E, 21F, as shown in FIG. 10. As air flows through the coarse mesh 22 large particulate can be captured and irradiated within the filter before exiting through fine mesh 24. Additionally, because of the reflective nature of the inside of the housing and baffles 26 or 26A the UV rays are thereby enhanced. Particles trapped within the filter will be bombarded with UV until destroyed, thereby causing the filters to be self-cleaning within the effective irradiation range. The filter housing is made of aluminum that is polished in order to get maximum UV reflectivity within the filter chamber. Further, the media filter on the output side of the filter chamber is made of fine aluminum mesh with a surface oxide for two important reason: (a) The ionization process within the chamber is assisted by the aluminum mesh, and (b) the media webbing of the filter catches (by ionization, electrostatic and barrier methods) and holds the particles/organic molecules so the UV irradiation breaks down the organic molecules, cleaning the filter surface of particulate collection.

The filter mesh is dipped/sprayed with a liquid mixture of water and sodium persulfate ($Na_2S_2O_8$), or potassium persulfate ($K_2S_2O_8$) or sodium hydroxide (NaOH). These liquid mixtures dry at room temperature on the surface of the mesh, leaving a residue of the persulfates or sodium hydroxide. The persulfates, when exposed to UV at wavelengths 100 nm to 320 um, form hydrogen peroxide ($H_2O_2$). Hydrogen peroxide, however, quickly breaks down into hydroxide ions (OH—) and water ($H_2O$) when exposed to these wavelengths. Under the alternative, the sodium hydroxide, when exposed to short wave ultraviolet, breaks down into sodium ions (Na+) and hydroxide ions (OH—).

Furthermore, by providing reflective baffles 26 and 26A that are polished aluminum positioned on the incoming air side wall, reflection is additionally enhanced. The geometries of the baffles 26 and 26A tend to reflect UV rays back toward the central portion of the chamber 34. The polishing of the aluminum baffles 26 and 26A reflect up to 90% of the UV striking the baffle surfaces and facilitate focusing the reflected UV on to the aluminum filter mesh for higher UV intensity on the fine mesh filter surface 24. The geometry of baffle 26 is a V-shaped channel with the vertex edge facing the incoming airstream while the legs are diverging outwardly downstream. The geometry of baffle 26A is a somewhat U-shaped channeled with the bight perpendicular to the incoming airstream and the legs diverging outwardly down stream. Also, the baffles 26 and 26A prevent direct UV light traveling back out the coarse mesh 22. As the air passes through the incoming opening, the baffles 26 and 26A angle the air toward the outer edges of the baffles, creating the venturi-effect and causing turbulence. This pulls the circulating air back over the edges of the baffles, next to the UV lamps (sitting in the partial vacuum). By also providing wall 42 and bottom wall 40 of a polished aluminum material, maximum reflective irradiation is achieved. The UV rays will either strike particulates directly or will be reflected about the chamber enhancing the irradiation bombardment. Certainly, by sizing the chamber 34 appropriately, it could be retrofitted within existing certain HVAC filter housings without modification to the existing housings. However, where an HVAC unit is of an unusual size, minor modifications may be rendered to so fit chamber 34.

Figure 9:
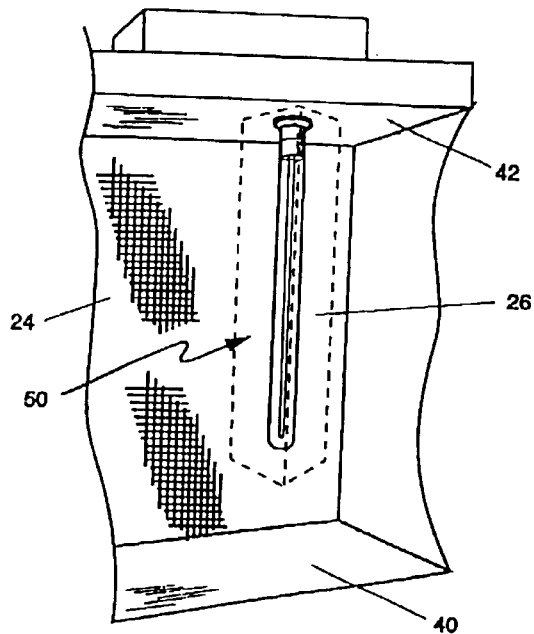
FIG. 9 is a cutaway view of the chamber of the invention showing rays bouncing off the V-shaped reflective baffles within the chamber of the invention.
Figure 9A:
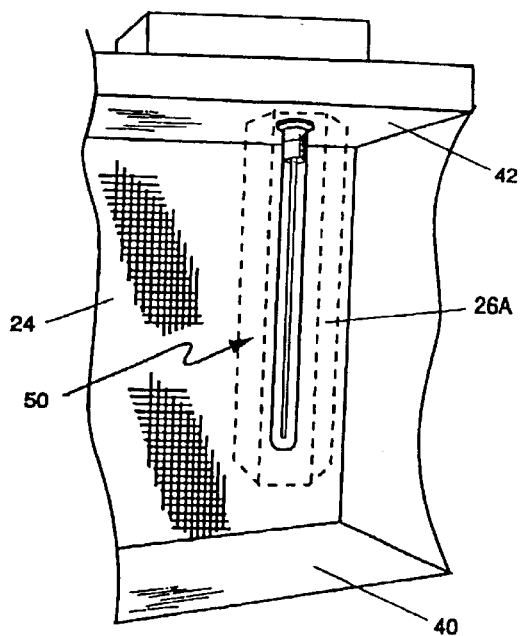
FIG. 9A is a cutaway view of the chamber of the invention showing rays bouncing off the somewhat U-shaped channeled baffles with the bight perpendicular to the airstream and the legs diverging outwardly down stream.

In use and operation, as viewed in FIG. 4, air A traveling through the duct work of a HVAC system will travel through a first aluminum filter 20 by way of its first coarse mesh 22 and then its first fine mesh 24. Thereafter, the air enters chamber 34 and as the air passes through the incoming opening, the baffles 26 and 26A angle the air toward the outer edges of the baffles, creating the venturi-effect. This pulls the circulating air back over the edges of the baffles, next to the UV lamps (sitting in the partial vacuum) and flows by UV lamps 50 thus increasing the amount of irradiation the passing air receives. The air then exits the actinism chamber 34 through another fine mesh 24 of second aluminum filter 23 and out through a second course mesh 22. Thereafter, having been irradiated and filtered, the air is returned to the HVAC ducts. Any particulate remaining in the second aluminum filter 23 will continue to be irradiated until destroyed by UV lamps 50 as seen in FIGS. 9 and 9A.

Installation of UV filter will be in the traditional location of current building central air filters: in the system return air ducts, cavity or plenum. The air is pulled through the return air ducts, cavity or plenum. The air is pulled through the return air ducts by the fan located in the furnace housing.

Incoming air passes through the incoming opening into the UV chamber of the filter housing. Mounted on the incoming side are several angled/curved polished aluminum baffles 26 or 26A running from top to bottom.

Figure 12:
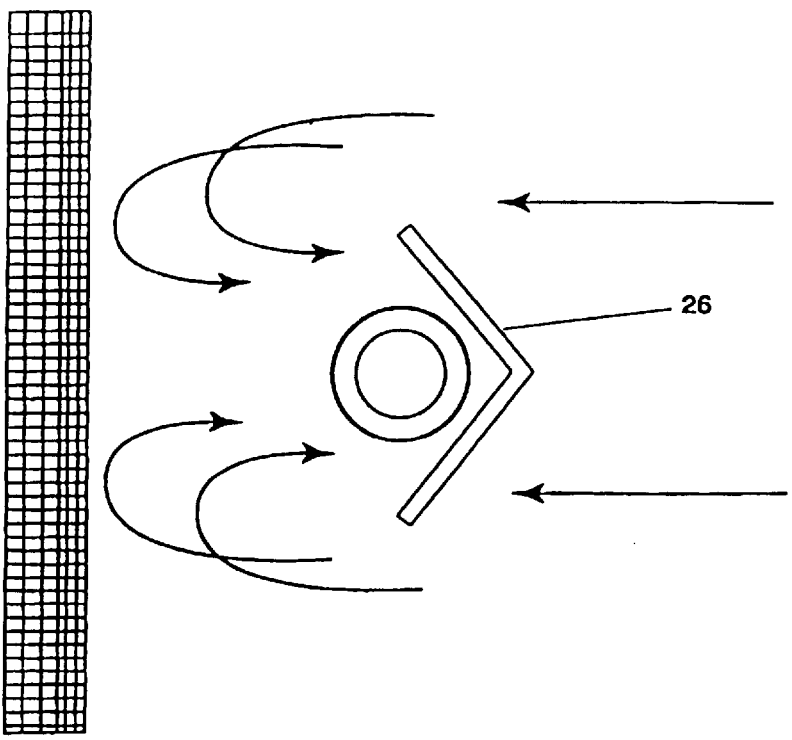
FIG. 12 is a top view of the baffle showing the venturi effect created by its insertion into the airstream.
Figure 12A:
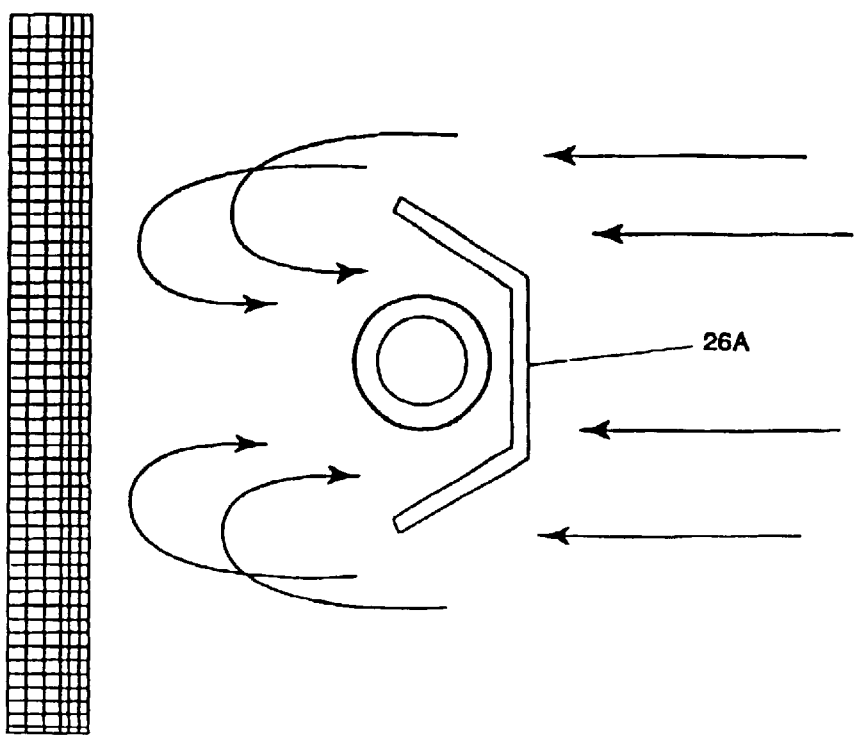
FIG. 12A is a top view of the alternative baffle showing the venturi effect created by its insertion into the airstream.

As the air rushes (indoor air in a system return duct moves about 200–300 fpm through the duct) through the incoming filter opening, the baffles 26 and 26A mounted inside this perforated wall, creates the venturi-effect. This results in the circulating air being pulled against each of the UV lamps mounted within the cavity of the angular baffles for maximum irradiation of passing air. See FIGS. 12 and 12A.

Each lamp 50 runs parallel to the baffle 26 or 26A and within the angular cavity of the baffle. See FIGS. 9 and 9A. The UV irradiation from the backside of the lamp projected toward the baffle 26 or 26A is reflected back out to the lamp area, increasing the UV intensity on the airborne particles that have been pulled by partial vacuum next to the lamp. Within inches of the lamps, all airborne microorganisms are irradiated with high intensity UVC (ultraviolet radiation in the short wave or C band range), leaving most airborne organisms killed. In addition, this high intensity UVC region strips electrons from the dead and dying organisms and other airborne organic particles.

Further, the highly polished aluminum baffles 26 or 26A reflect up to 90% of the UV irradiation to the opposite filter mesh wall 22. This bathes the mesh with up to 90% more UV irradiation than would be present directly from the lamps. The higher intensity at the filter mesh helps to break down the dust and biological materials collecting on the filter mesh at a faster rate.

Ultraviolet photons emitting from the lamps 50 with the short/medium wavelength ultraviolet light starts the electron stripping and ionization process of air passing through the actinism chamber 34 because the incoming air is populated with airborne biological and organic dust.

Airborne organic molecules (compounds made of carbon, hydrogen, oxygen and nitrogen) have high absorption (decay) rate when exposed to short/medium wavelength UV in the order of 230 nm–320 nm. The process of organic decay starts when UV irradiates the airborne organic or biological particles, stripping the material of electrons. The particles become positively charged or ionized.

The process of electron stripping, within the present invention's UV filter, has a direct effect upon circulating airborne organic and biological materials circulating and growing within the central air system. It begins when the circulating air (populated with organic and biological materials) is pulled though the filter 20 and immediately to each individual UV lamp 50 as the result of the baffles 26 and 26A causing an eddy current of turbulence which creates a partial vacuum. The intensity in the immediate area of the lamp is elevated by the baffle reflectivity of secondary UV. As airborne organic molecules are exposed to the UV lamp 50, electrons are stripped from the materials and the decay begins, leaving most of the airborne particles positively charged.

The airborne charged particles continue to be pulled to the opposite wall of the actinism chamber 34 by the system fan (e.g. 46 in FIG. 6) further downstream from the filter 23. The filter 23 contains two porous aluminum mesh filters, the coarse mesh 22 and fine mesh 24 so the air to can continue unabated through the filter and on to the blower assembly. The filter mesh has been previously sprayed with or dipped into a liquid sodium persulfate, potassium persulfate or sodium hydroxide mixture. The mixture, once dried will form crystals on the mesh material.

As the air continues through the filter mesh 23, the aluminum oxide fibers pick up the charged organic and biological materials coming from the UV light and baffle area. The organic material adheres to the aluminum mesh for several reasons.

The filter mesh material is an aluminum alloy that is extremely tough due to an impervious film of oxide on the metal. But any material can be used that is combined with an oxide. The aluminum oxide mesh is preferred because of two reasons: (a) The aluminum is excellent for reflecting the ultraviolet within the filter chamber resulting in UV amplification, with little or no deterioration on the metal itself. (b) The oxide film in the metal has a high propensity to collect electrons that generates an electrostatic polarity. This produces an affinity for either negative or positive ions (depending upon the pH) to the filter mesh. Aluminum oxide has the highest advantage over all solid material because it is very stable over the wide range of pH. Normally the pH on the filter surface will be relatively high from the decay of organic materials on the filter, thus attracting positive ions to the mesh.

The process on the aluminum oxide mesh is called electronegativity, which forms the basis electrostatic energy on the filter surface. Electronegativity is based upon the principle of the power of an atom in a molecule to attract electrons to itself. The electronegativity of an element depends upon its valence state. Aluminum has an average electronegativity value of 1.61 (near the middle compared to the other element values in the group); oxygen has the second highest value of all elements to attract electrons to itself at 3.44. The filter, made of fibrous aluminum/oxide metal, has a very high attraction ability of free electrons to the webbing, primarily due to the strength of the oxide (oxygen) to attract elections.

The aluminum oxide filter has an enormous capacity to attract an abundance of free electrons that the UV stripped from the incoming organic and biological particles near the baffles. As the aluminum oxide collects more and more electrons, the filter mesh loads up on electrons, becoming primarily negative.

And as the positively charged organic ion material (coming from the UV light area) nears the negatively charged filter, the organic molecules begin adhering to the mesh's webbing based upon the principle of positive/negative polarity (the electrostatic principle). In other words, the incoming airborne positively charged organic materials are attracted to the negatively charged webbing and adhere to the filter mesh.

But the electron stripping at the lamp and collection at the filter mesh is just the primer to start a very dynamic process. The process becomes a chain reaction with the formation of Hydroxide(OH—)/Hydroxyl(OH) on the filter mesh in two ways: (a) when organic compounds break down in the presence of UV, one of the byproducts is water ($H_2O$). Water is exposed to short wave UV can form Hydroxyl (OH). (b) The dried crystals of persulfates within the filter mesh, when exposed to UV form hydrogen sulfate and hydrogen peroxide ($S_2O_8^{-2}+2H_2O+UV=2HSO_4^{-}+H_2O_2$). The hydrogen peroxide ($H_2O_2$) both hydroxide (OH—) and water in the presence of UV ($H_2O_2+UV=H_2O+OH$).

The UV intensity on the filter mesh 23 is extremely high due to the direct ultraviolet of the UV lamps and baffle UV reflectivity focused on the filter. With the organic material collecting the filter webbing 21, see FIG. 10, the UV irradiation has plenty of dwell time to complete the break down process on the larger collected particles. The primary purpose of the filter mesh is to collect the organic material so the UV can decay the organic material, resulting primarily -in airborne carbon, oxygen, hydrogen and nitrogen. There will be also be traces of $H_2O$ (water) and $CO_2$ (carbon dioxide) formed as the result of the breakdown process of the organic materials. Thus cleaning the mesh surface 21, as well as decaying airborne toxins and germs.

An operating actinism chamber 34 is a very dynamic environment with many physical and chemical processes going on simultaneously, all started by high intensity short/medium UV radiation. The filter baffles 26 or 26A create eddies that pull the incoming air up against the UV lamps located within the baffle's cavity. The high intensity ultraviolet strips electrons from the airborne organic and biological materials. By losing electrons, the organic material becomes positively charged material. An abundance of free electrons collect within the filter chamber on accelerated bases as more material is exposed to UV radiation. In the meantime, the aluminum oxide filter mesh 23 has high propensity to absorb free electrons. As the aluminum oxide filter webbing 21 collect more and more electrons, the mesh gains a negative charge. The negative charge on the filter surface then gains polarity with the positive airborne organic particles, collecting the particles on the filter surface.

The formation of hydroxide ions from either the persulfates reaction (persulfates to hydroperoxides converting to hydroxide in the presence of short wave to medium wave UV) presents a stable but a very potent one-election oxidant. The reason is that hydroxide is destructive to organic molecules because it "steals" hydrogen molecules from the organic materials, leaving decayed carbon ions.

The "theft" of hydrogen from organic molecules by hydroxyl radicals forms even stronger OH bonds, with even higher oxidation, as the result of water and hydroperoxide on filter mesh. The hydroxyl oxidation process turns into a chain reaction on the filter mesh the breakdown and formation of new radicals results in continual decay of the organic material on the filter.

Figure 6:
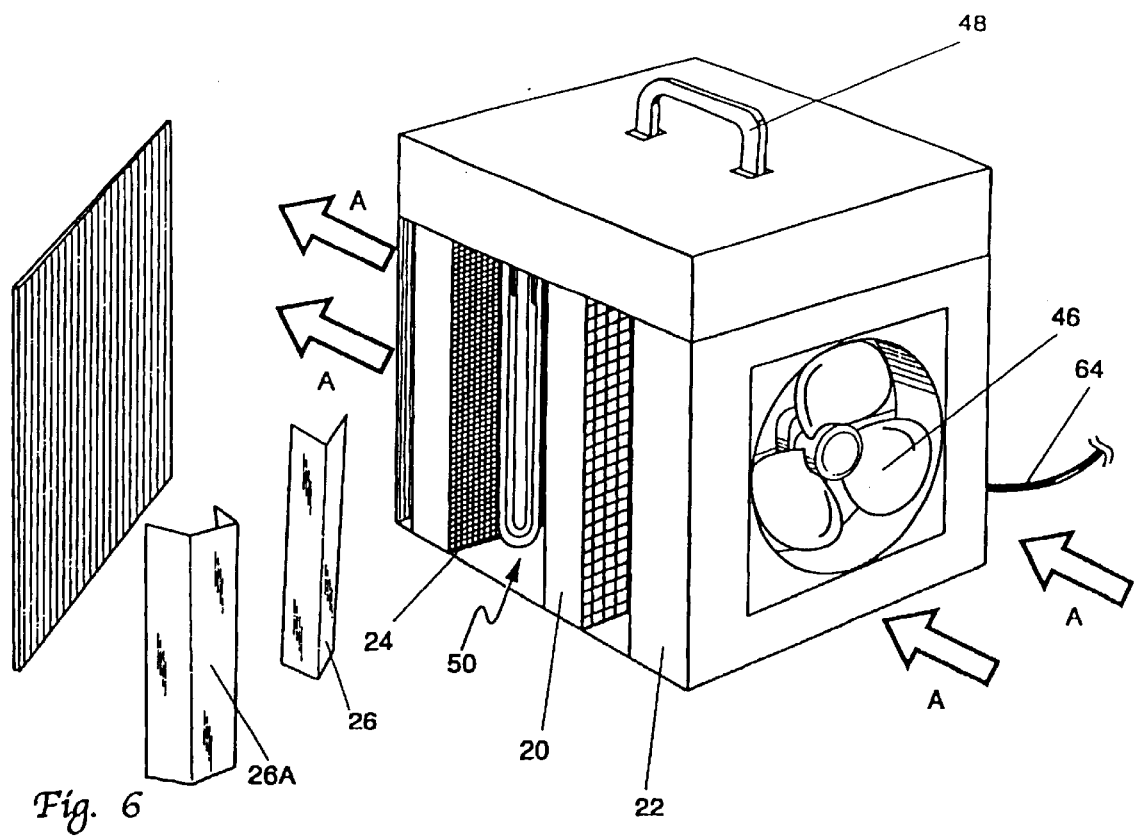
FIG. 6 is a perspective view of a portable alternate embodiment of the invention with a side panel off and the two alternative reflective plates projected.

The above-described configuration is ideal for insertion into the return of an HVAC system. FIG. 6 depicts a similar, but alternative embodiment for portable use within a room. Fan 46 provides for the air flow A of this portable device through similar but smaller aluminum filters 20. Between the filters 20, again are maintained one or more UV lamps 50. To transport this item, handle 48 is also provided. Reflective enhancement of the radiation is likewise caused by a plurality of polished aluminum surfaces throughout the inside of the chamber. This is an ideal apparatus for cleaning the air in a single room.

Figure 7:
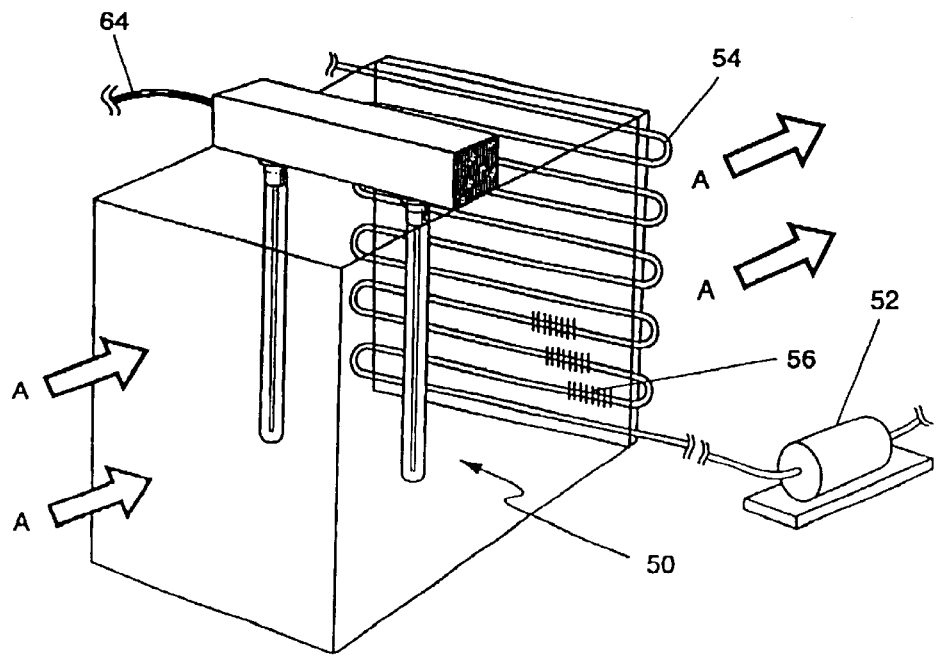
FIG. 7 is a perspective view of an external alternate embodiment of the invention.

FIG. 7 depicts another alternate embodiment for use with an external HVAC device. An evaporative coil 54 having fins 56 is coupled to a typical compressor 52 thereby is depicted in FIG. 7. To prevent contamination build-up and to destroy contamination build-up on or about coil 54 UV lamp or lamps 50 are mounted near coil 54. By continuing the lamps 50 in an "on" setting, and additionally using the reflective properties of the aluminum fins 56, any contamination on or near the coils is eliminated. The fins 56 are preferably wetted with sodium persulfate, potassium persulfate or sodium hydroxide and then dried forming a crystalline skin. By maintaining this area in a clean manner, air flow over the area and into the duct work of an HVAC system will be less likely to carry such contamination. In the alternative to this embodiment, baffles 26 and 26A could be placed in such a configuration whereby the UV lamps 50 are contained within the cavity formed by the baffling such that the air is diverted around the UV lamps 50. This geometry would yield similar results to the geometry for the embodiments described supra and shown in FIGS. 2 through 6 and 12 and 12A.

Figure 13:
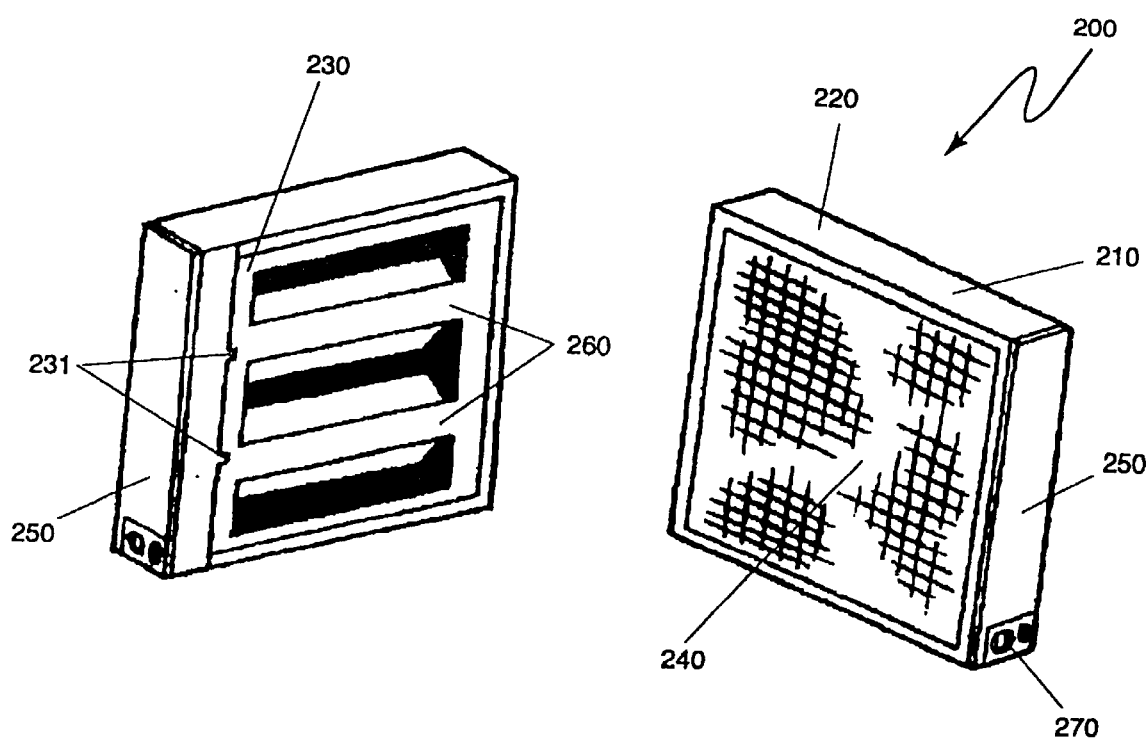
FIG. 13 is an alternative embodiment of the filter of the invention.

FIG. 13 shows an alternative embodiment 200 of the invention. A filter cassette 210 includes an air outlet plate 220 and an air inlet plate 230. The air outlet plate 220 is mainly constructed of the filter mesh 240. The air inlet plate 230 is formed from a piece of planar material. During the manufacturing of the air inlet plate 230, the planar material is incised at particular positions within the material. The incisions produced during the manufacturing process permit portions of the material to be bent in a manner to form the baffling 260. This baffling is analogous to the shapes shown in FIGS. 12 and 12A for baffling 26 and 26A. The bulbs 50 (not shown) are behind the baffling 260 and in this configuration generates analogous results as the baffling 26 and 26A described supra. The air inlet plate 230 is hinged at 231 to permit access to the interior of the cassette. Below the removable side panel 250 is a standard 115 vac outlet 270 for supply power to the bulbs 50.

Figure 14A:
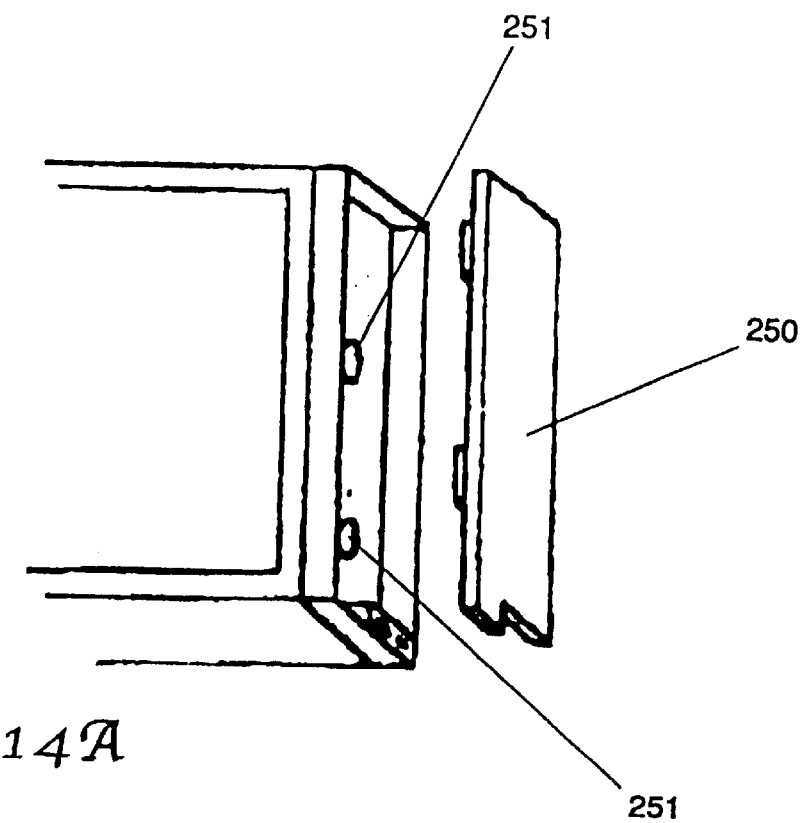
FIG. 14A is view showing the removal of a side panel.
Figure 14B:
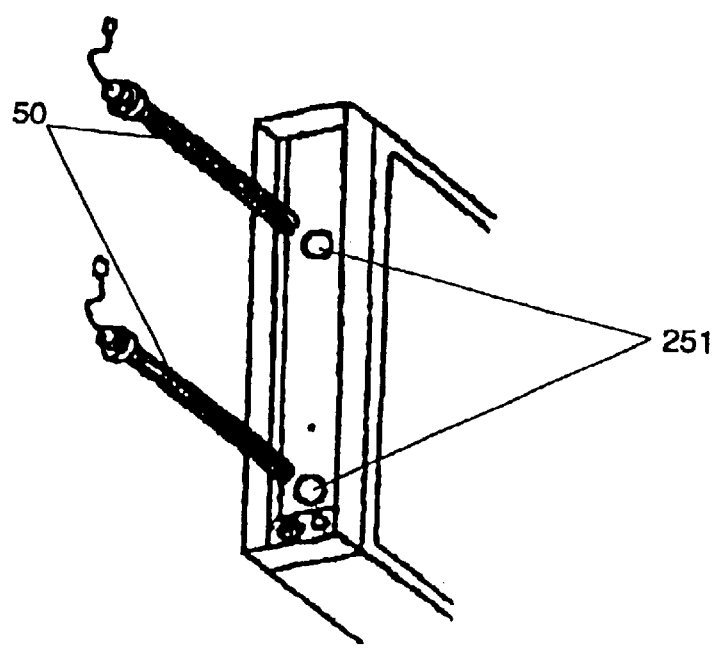
FIG. 14B shows a view of the light bulbs being inserted.

FIGS. 14A and 14B show the removable side panel 250 have been remove and exposing holes 251 for the bulbs 50 to be inserted therein such that the bulbs 50 would be proximate the baffling 260 and within the filter cassette 210. This arrangement permits ease of bulb replacement and filter cassette cleaning.

Figure 15:
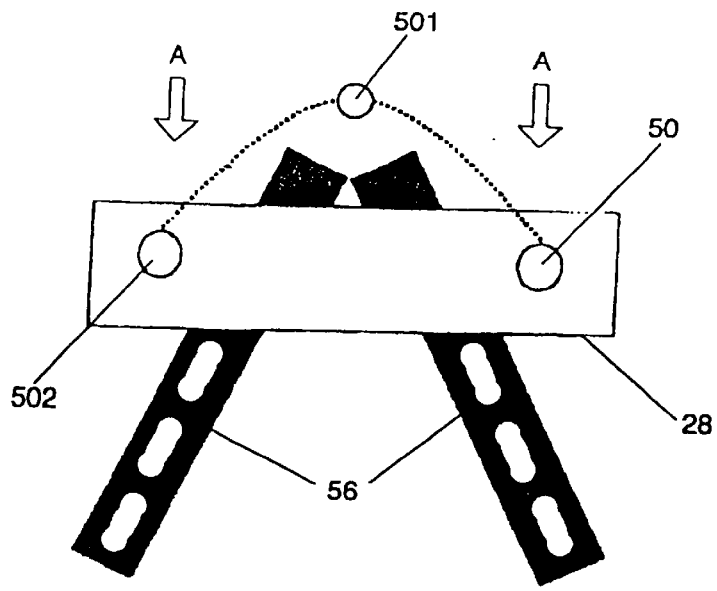
FIGS. 15A, B, and C show an alternative bulb and coil positioning of the invention.
Figure 15:
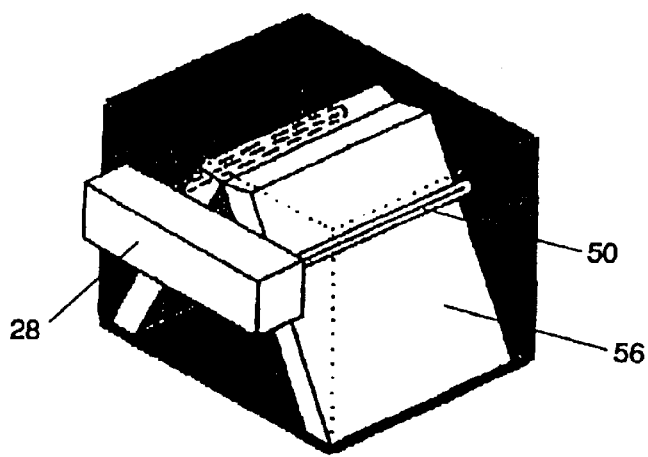
Figure 15:
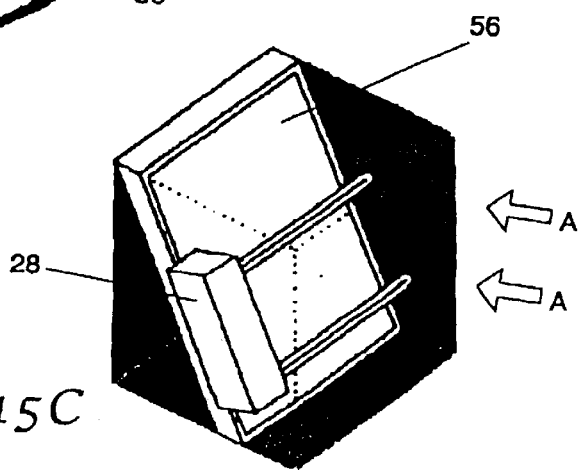

FIGS. 15A and 15B show the arrangement of bulbs 50 relative to a coil installation where the coils 56 are positioned in a "V" configuration. While in FIG. 15C, the figure shows the arrangement of the housing 28 with bulbs 50 relative to a coil installation where the coil 56 is at a slant within the chamber the coil 56 is installed within. The interrelation between the bulbs 50 and coils 56 is that the bulbs are positioned on the upstream side of the coils. However, alternatively the bulbs 50 could be positioned on the downstream side of the coils 56. For the best exposure to the coil 56 the bulbs 50 should be at least six inches away from the coil or coils 56.

Figure 16A:
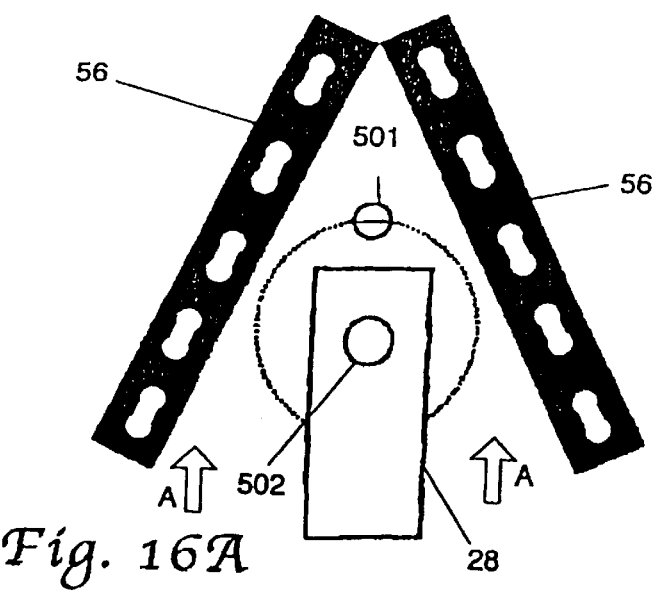
FIGS. 16A, B, and C show another alternative bulb and coil positioning of the invention.
Figure 16B:
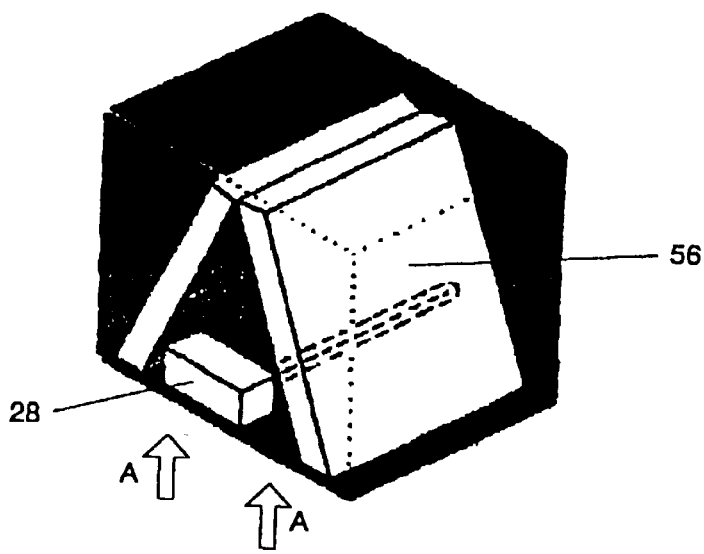
Figure 16C:
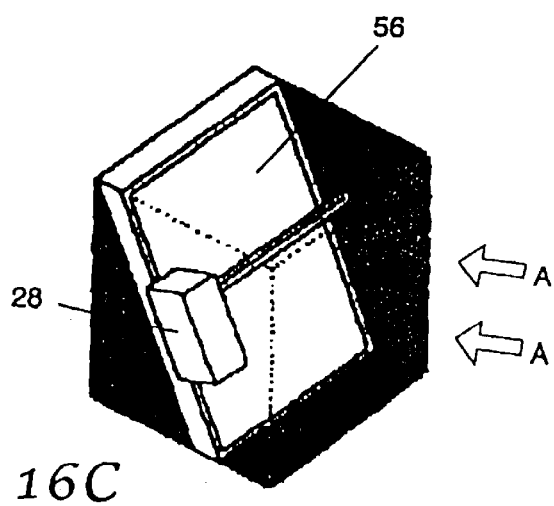

Likewise FIGS. 16A and 16B show the arrangement of bulb 50 relative to a coil installation where the coils are positioned in a "V" configuration. While in FIG. 15C, the figure shows the arrangement of the housing 28 with bulb 50 relative to a coil installation where the coil 56 is at a slant within the chamber the coil 56 is installed within. The interrelation between the bulb 50 and coils 56 is that the bulb 50 is positioned on the upstream side of coil 56. For the best exposure to the coil 56 the bulb 50 should be at least six inches away from the coil or coils 56.

For the installations shown in FIG. 15A through 16C, viewpoint 501 should be drilled anywhere in a direct line of sight of the hole or holes 502 for the bulbs 50.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A chamber for cleansing ambient air, comprising, in combination:
   an air inlet;
   an air outlet;
   said chamber interposed and communicating between said inlet and outlet;
   a source of radiation in said chamber, said chamber having an interior surface with means for reflecting substantially all the radiation; and
   a coating means in said chamber to enhance the effect of the radiation.

2. The chamber of claim 1 wherein said coating means is a persulfate or a hydroxide.

3. The chamber of claim 1 wherein said reflective means comprises polished aluminum coextensive with said interior surface of said chamber.

4. The chamber of claim 3 further comprising a plurality of filters slideably mounted about said radiation source.

5. The chamber of claim 4 wherein said filters have restrictive means on a surface of facing said radiation source.

6. The chamber of claim 5 wherein said restrictive means is a finely woven mesh having a coarsely woven mesh on an opposite side of said filter.

7. The chamber of claim 6 wherein said filters are made of polished aluminum.

8. The chamber of claim 7 wherein said interior surface is formed from two side walls coupled to an upper wall and said filters lie normal to the air path and perpendicular to said walls.

9. The chamber of claim 1 wherein adjacent said source of radiation is a baffling means for creating turbulence around said source when ambient air passes between said inlet and said outlet.

10. The chamber of claim 9 wherein said baffling means has a geometry that partially encloses said radiation sources.

11. The chamber of claim 5 wherein said coating is adjacent said filters.

12. The chamber of claim 1 wherein said inlet and said outlet are enclosed by fillers, said filters coated with a catalyst to react with radiation from said source.

13. The chamber of claim 12 wherein said radiation is ultraviolet.

14. The chamber of claim 12 wherein said catalyst is sodium persulfate.

15. The chamber of claim 12 wherein said catalyst is potassium persulfate.

16. The chamber of claim 12 wherein said catalyst is sodium hydroxide.

17. The chamber of claim 12 wherein said chamber is located in an HVAC environment including an evaporative coil and fan in fluid communication with said chamber.

18. The chamber of claim 17 wherein said coil is coated with said catalyst.

19. The chamber of claim 17 wherein said filters are formed from mesh and said radiation source is adjacent a baffle.

20. The chamber of claim 1 further including an evaporative coil adjacent said source of radiation, said coil coated with a catalyst to react with radiation from said source.

21. The chamber of claim 20 wherein said radiation is ultraviolet light.

22. The chamber of claim 20 wherein said catalyst is sodium persulfate.

23. The chamber of claim 20 wherein said catalyst is potassium persulfate.

24. The chamber of claim 20 wherein said catalyst is sodium hydroxide.

25. The chamber of claim 20 wherein said chamber is located in an HVAC environment.

26. The chamber of claim 20 wherein said radiation surface is protected by a baffle causing turbulence around said source.

27. The chamber of claim 1 wherein said coating means is selected from the group including persulfates and hydroxides.

28. The chamber of claim 1 wherein said coating means behaves according to the reaction $S_2C_8^{-2}+2H_2O+UV=2HSO_4^-30\ H_2O_2$ if said coating means is a persulfate.

29. An apparatus for purging impurities from ambient air conditions, comprising, in combination:

a source of radiation in operative communication with the ambient air conditions; and wherein said source is upstream from an evaporative coil or a filtering means.

30. The apparatus of claim 29 further comprising: a coating upon which radiation-emitted from said source impinges thereon facilitating a chemical reaction.

31. The apparatus of claim 30 wherein said coating is on said coil or filtering means.

32. The apparatus of claim 31 further comprising a viewing port proximate said source.

33. The apparatus of claim 32 wherein said coil is of a substantially "V" shape.

34. The apparatus of claim 33 wherein said coil is positioned at an angle not perpendicular to a flow of air across said coil.

35. A chamber for cleansing ambient air, comprising, in combination:

a source of radiation in said chamber;

means for directing the ambient air past said radiation source;

and a catalyst adjacent said radiation source to enhance the effectiveness of the radiation, said catalyst is either a persulfate or a hydroxide.

36. The chamber of claim 35 wherein said catalyst behaves according to the reaction $S_2O_8^{-2}+2H_2O+UV=2HSO_4^-+H_2O_2$ if said catalyst.

37. An apparatus for purging impurities from ambient air conditions, comprising, in combination:

a source of radiation in operative communication with ambient air, said ambient air containing moisture, wherein said source is upstream from an evaporative coil or a filtering means, said evaporative coil or filtering means having means for extracting and retaining said moisture from said ambient air.

38. A chamber for cleansing ambient air, comprising, in combination:

a source of radiation in said chamber;

means for directing the ambient air past said radiation source, the ambient air containing moisture; and a catalyst adjacent said radiation source to enhance the effectiveness of the radiation and for retaining said moisture from said ambient air in said chamber, said catalyst is either a persulfate or a hydroxide.

39. A clamber for cleaning ambient air containing moisture, comprising, in combination:

an air inlet;

an air outlet;

said chamber interposed and communicating between said inlet and outlet;

a source of radiation in said chamber, said chamber having an interior surface with means for reflecting substantially all the radiation; and a coating means in said chamber to enhance the effect of the radiation and to enhance extraction and retention of moisture in said ambient air.

* * * * *